(12) United States Patent
Moore et al.

(10) Patent No.: US 7,967,828 B2
(45) Date of Patent: Jun. 28, 2011

(54) GRAVITY FEED IMPLANT DISPENSER

(75) Inventors: Jesse Gabriel Moore, Swartz Creek, MI (US); Jeffrey W. Beale, Bartlett, TN (US); Rodney Ray Ballard, Lakeland, TN (US)

(73) Assignee: Warsaw Orthopedic, INc., Warsaw, IN (US)

( * ) Notice: Subject to any disclaimer, the term of this patent is extended or adjusted under 35 U.S.C. 154(b) by 1034 days.

(21) Appl. No.: 11/635,098

(22) Filed: Dec. 7, 2006

(65) Prior Publication Data

US 2008/0140086 A1 Jun. 12, 2008

(51) Int. Cl.
*A61B 17/88* (2006.01)

(52) U.S. Cl. .................. 606/99; 606/86 A; 606/104

(58) Field of Classification Search .............. 42/1.02, 42/11, 15, 27, 39.5; 606/99, 142, 143, 916, 606/62, 75, 104, 86 A; 81/57.23, 57.37, 81/433, 435; 221/13, 179, 181, 198, 235, 221/264, 268, 309; 411/15, 17
See application file for complete search history.

(56) References Cited

U.S. PATENT DOCUMENTS

| | | | | |
|---|---|---|---|---|
| 1,507,775 A * | 9/1924 | Hoehn | | 227/138 |
| 1,537,929 A | 5/1925 | Lee | | |
| 2,247,500 A | 7/1941 | Hutchison, Jr. | | |
| 2,620,061 A * | 12/1952 | Uxa | | 221/229 |
| 2,939,146 A * | 6/1960 | Abrams | | 227/120 |
| 3,630,428 A * | 12/1971 | Olney et al. | | 227/128 |
| 4,040,556 A * | 8/1977 | Dahle | | 227/120 |
| 4,216,878 A * | 8/1980 | Naud | | 221/264 |
| 4,311,251 A * | 1/1982 | Sternberg | | 221/24 |
| 4,478,112 A * | 10/1984 | Moulton | | 81/57.37 |
| 4,811,647 A | 3/1989 | Lindamood | | |
| 4,958,873 A | 9/1990 | Akagawa | | |
| 4,963,144 A | 10/1990 | Huene | | |
| 5,352,231 A | 10/1994 | Brumfield et al. | | |
| 5,437,211 A | 8/1995 | Wolfe | | |
| 5,445,641 A * | 8/1995 | Frigg et al. | | 606/86 R |
| 5,484,440 A * | 1/1996 | Allard | | 606/916 |
| 5,590,574 A * | 1/1997 | Lide | | 81/124.1 |
| 5,649,931 A | 7/1997 | Bryant et al. | | |
| 5,735,854 A | 4/1998 | Caron et al. | | |
| 5,791,207 A | 8/1998 | Ahdoot | | |
| 5,941,885 A * | 8/1999 | Jackson | | 606/104 |
| 6,112,944 A | 9/2000 | Van Hoorn et al. | | |
| 6,129,730 A | 10/2000 | Bono et al. | | |
| 6,132,435 A | 10/2000 | Young | | |
| 6,139,549 A * | 10/2000 | Keller | | 606/86 A |
| 6,189,422 B1 * | 2/2001 | Stihl | | 81/452 |
| 6,224,596 B1 | 5/2001 | Jackson | | |
| 6,273,893 B1 | 8/2001 | McAllen, III et al. | | |
| 6,283,973 B1 | 9/2001 | Hubbard et al. | | |
| 6,328,746 B1 | 12/2001 | Gambale | | |
| 6,634,261 B1 | 10/2003 | Griffin | | |
| 6,974,466 B2 | 12/2005 | Ahmed et al. | | |

(Continued)

FOREIGN PATENT DOCUMENTS

DE 298 16 215 U1 11/1998

(Continued)

*Primary Examiner* — Eduardo C Robert
*Assistant Examiner* — Christian Sevilla (57) ABSTRACT

Instruments and methods are provided for delivering multiple implants to multiple implant locations in a patient without requiring a second implant to be loaded onto or engaged to the delivery instrument after delivery of a first implant. The implants can be sequentially engaged, using the delivery instrument, to the patient or to receptacles of one or more receiving members secured to the patient.

20 Claims, 10 Drawing Sheets

U.S. PATENT DOCUMENTS

| | | |
|---|---|---|
| 7,147,641 B2 | 12/2006 | Chen |
| 7,179,261 B2 * | 2/2007 | Sicvol et al. .................. 606/86 A |
| 7,240,588 B1 | 7/2007 | Rinner |
| 7,451,893 B2 | 11/2008 | Martin |
| 2002/0099386 A1 | 7/2002 | Beger et al. |
| 2002/0193807 A1 | 12/2002 | Chen |
| 2004/0243139 A1 * | 12/2004 | Lewis et al. .................... 606/104 |
| 2005/0149031 A1 | 7/2005 | Ciccone et al. |
| 2005/0192570 A1 * | 9/2005 | Jackson ........................... 606/61 |
| 2005/0203530 A1 | 9/2005 | Oribe et al. |
| 2005/0222575 A1 | 10/2005 | Ciccone et al. |
| 2006/0027592 A1 | 2/2006 | Flamingo et al. |
| 2007/0088363 A1 | 4/2007 | Rezach |
| 2007/0276403 A1 | 11/2007 | Franks et al. |
| 2008/0255576 A1 | 10/2008 | Protopsaltis |

FOREIGN PATENT DOCUMENTS

| | | |
|---|---|---|
| FR | 668187 | 10/1929 |
| GB | 2 355 505 A | 4/2001 |
| WO | WO 94/12111 | 6/1994 |
| WO | WO 02/45595 A2 | 6/2002 |

* cited by examiner

GRAVITY FEED IMPLANT DISPENSER

BACKGROUND

Various types of devices and systems have been used for positioning implants into a patient in surgical procedures. Spinal stabilization systems have employed plating systems, rods, anchors, fusions devices, artificial discs, and other implants along or in the spinal column for rigid, dynamic, and semi-rigid spinal stabilization procedures. Such systems often include multiple implant members that must be engaged for the system to be properly installed. There remains a need for instruments and methods for delivering multiple implants to the implantation location while minimizing the time and complexity associated with handling and securing such implants during surgery.

SUMMARY

Instruments and methods for positioning multiple implants in surgical procedures include an instrument for delivering multiple implants configured to permit sequential securement of the implants in multiple receptacles of one or more receiving members or at multiple locations in the patient. The delivery instruments and methods permit implantation of multiple implants without any requirement for re-loading or re-engaging a second implant to the instrument after delivery of a first implant.

In one form, a surgical system includes a patient implantable receiving member including at least one receptacle. The system further includes an instrument including a handle member extending along a longitudinal axis and defining a passage and a compartment extending therein in side-by-side relation from a proximal end of the handle member toward a distal end. Also included is an actuating member extending transversely across the passage and the compartment adjacent to the distal end. The system further includes a guide shaft engaging with and extending distally from the handle member in axial alignment with the passage. A plurality of implants is positioned in the compartment with the actuating member being structured to move one of the plurality of implants from the compartment to the passage and into alignment with the guide shaft. The implant is fed toward a distal end of the guide shaft and is engageable with the receptacle of the receiving member when delivered from the distal end of the guide shaft.

In another form, a surgical system includes an instrument including an elongated handle member, a guide shaft engaged with and extending distally from the handle member, and an actuating member coupled with the handle member and extending transversely across the handle member. The actuating member communicates with a compartment and a passage defined by the handle member and is slidable therebetween to individually deliver a plurality of implants stored in the compartment from the compartment to the passage wherein the passage is aligned with the guide shaft. A driver instrument is positionable within the passage and through the guide shaft to engage the respective implant in the guide shaft.

In yet another form, a surgical instrument for delivering multiple implants to an implantation location is provided. The instrument includes a handle member including a side wall extending longitudinally from a proximal end wall to a distal end wall. The handle member defines an internal bore extending therethrough from the proximal end wall to the distal end wall. The handle member further defines a dividing wall separating the internal bore from an implant compartment. The handle member further includes a transverse pocket extending through the side wall at a side wall opening and communicating with the internal bore and the implant compartment. A guide shaft is further provided engaging with and extending distally from the distal end wall of the handle member. The guide shaft includes an internal bore aligned with the internal bore of the handle member and the internal bore of the guide shaft extends to a distal end opening. The instrument further includes an actuating member including an implant channel structured to individually house a respective implant of a plurality of implants stored in the implant compartment. The actuating member is translatable in the transverse pocket from a first position where the implant channel is aligned with the implant compartment to receive the respective implant to a second position where the implant channel is aligned with the internal bore for delivering the implant.

In a further form, a surgical method includes engaging at least one receiving member to a bony structure in a patient; positioning a distal end of a delivery instrument adjacent a first receptacle in the at least one receiving member; positioning an actuating member of the delivery instrument to locate a first implant from an implant compartment of the delivery instrument to a passage of the delivery instrument located adjacent to and in side by side relation to the implant compartment; and feeding the first implant from the passage along a guide shaft of the delivery instrument to the distal end.

Related features, aspects, embodiments, objects and advantages of the present invention will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Positioning of multiple implants during a surgical procedure is facilitated by a delivery instrument that includes a guide shaft coupled to a handle member in alignment with a passage extending through the handle member. The handle member includes an implant compartment adjacent the passage and an actuating member disposed in a recess extending transversely across the implant compartment and passage. The actuating member is structured to move an implant from the implant compartment to the passage for delivery through the passage to a respective implantation location within the patient during the surgical procedure without a requirement to withdraw the instrument and load or engage a second implant to the delivery instrument after delivery of a first implant.

Figure 1:
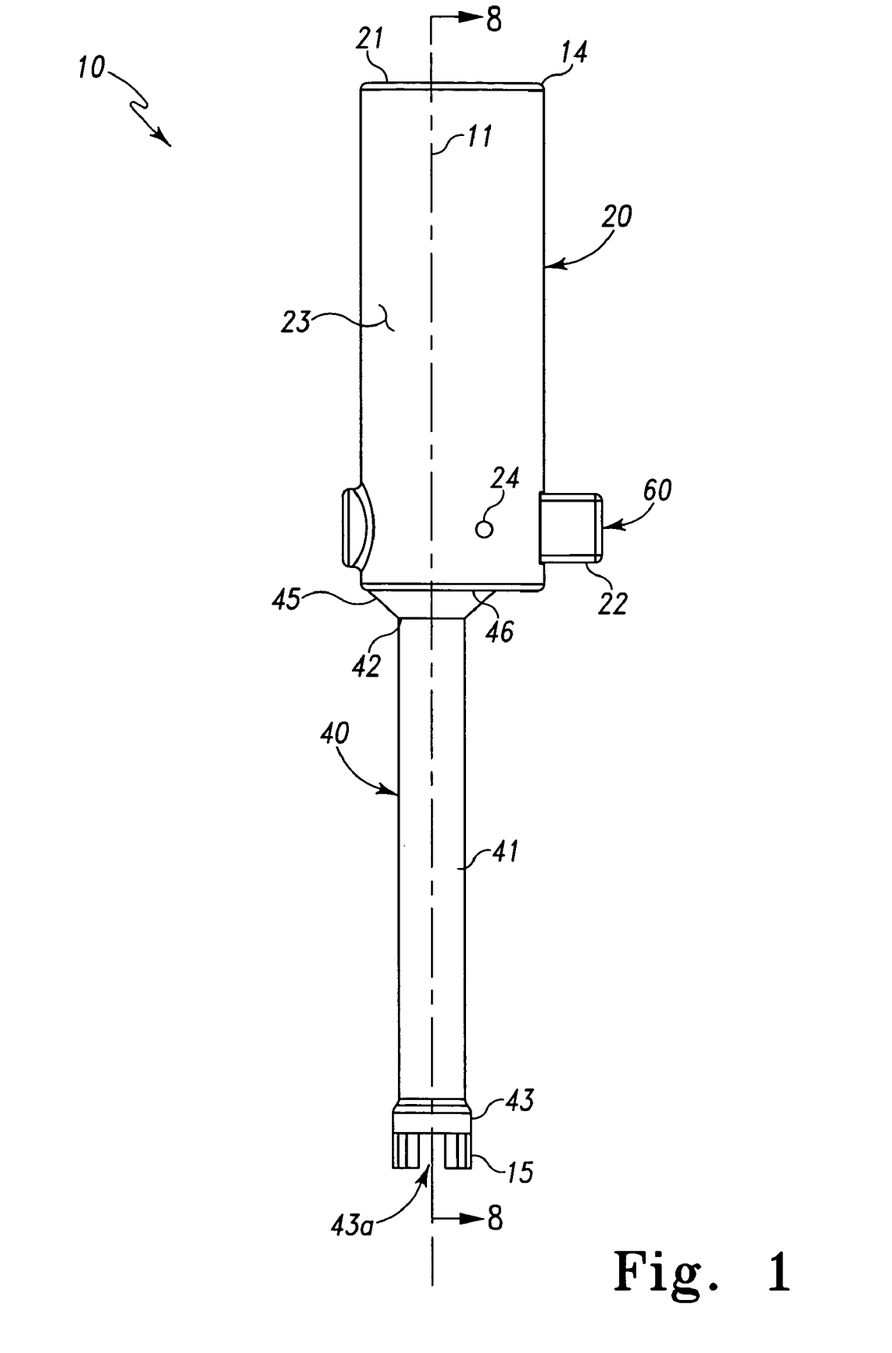
FIG. 1 is a side view of one embodiment of an implant delivery instrument.
Figure 2:
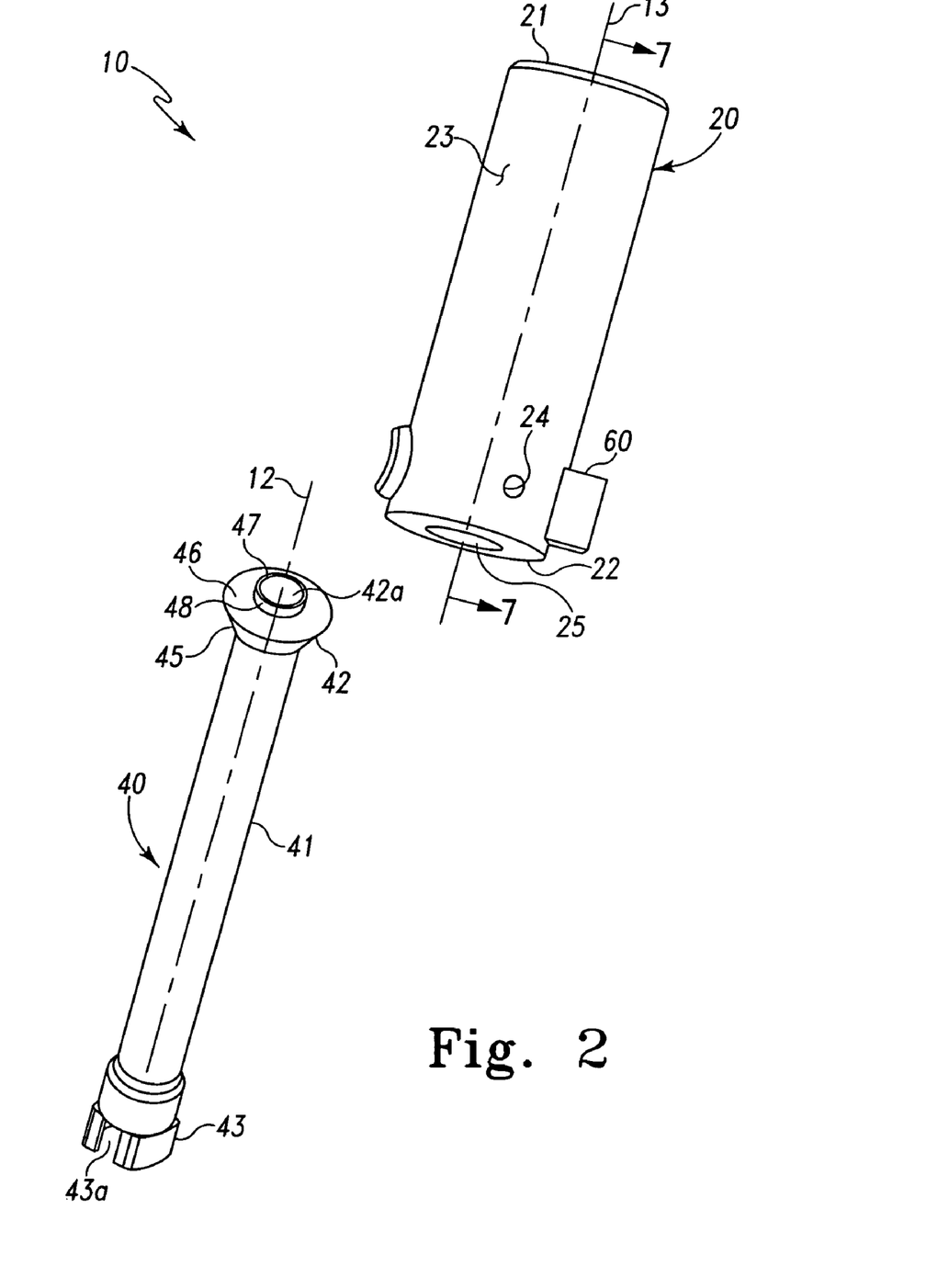
FIG. 2 is a partially exploded perspective view of the implant delivery instrument of FIG. 1.

In FIGS. 1-2 there is shown a delivery instrument 10 extending along a longitudinal axis 11 from a stock end 14 to a delivery tip 15 and including a handle member 20, a guide shaft 40, and an actuating member 60. Handle member 20 includes a proximal end wall 21 opposite a distal end wall 22, with a side wall 23 extending longitudinally between end walls 21 and 22 along handle axis 13, as shown in FIG. 2. Side wall 23 includes a thru-hole 24 extending therethrough while end wall 22 includes a guide shaft engaging opening 25.

Guide shaft 40 generally includes an elongated body 41 extending between a proximal end 42 and a distal end 43. Distal end 43 includes a distal end opening 43a structured to facilitate delivery of implants 100, as first shown in FIG. 8, to the implantation location. Guide shaft 40 is releasably engageable with handle member 20 for providing, in one specific instance, cleaning or autoclaving of guide shaft 40 individually after insertion thereof at the implantation location. Or, alternatively, in one embodiment, guide shaft 40 may be disposable after each operative use.

The external wall of body 41 is flared outwardly at proximal end 42 to form a handle member engagement fitting 45 structured to engage with opening 25. Fitting 45 includes an upper flat 46 encircling a collar 47 extending proximally from guide shaft 40. Collar 47 is formed about a proximal end opening 42a and may include a tapered section 48 thereon. When guide shaft 40 includes tapered section 48, opening 25 will include a reverse fitting tapered section (not shown) such that tapered section 48 mates therewith to provide a press fit engagement between guide shaft 40 and handle member 20 with upper flat 46 in contact with end wall 22, as shown in FIG. 1. It is contemplated that guide shaft 40 may be coupled to handle member 20 by any suitable configuration, including for example, a threaded engagement, a ball and socket engagement, a tooth and notch engagement, or a fused engagement, just to name a few. Furthermore, in an alternative embodiment not shown, guide shaft 40 may be formed integrally with handle member 20 as a single piece.

Figure 3:
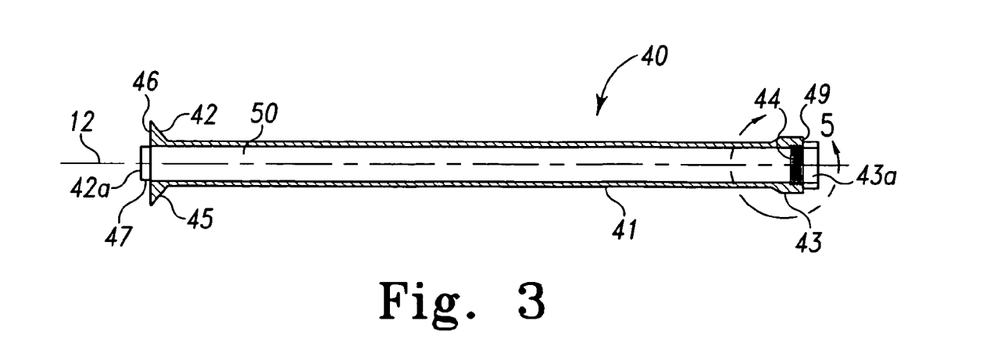
FIG. 3 is a longitudinal section view of the guide shaft of the delivery instrument of FIG. 1.
Figure 4:
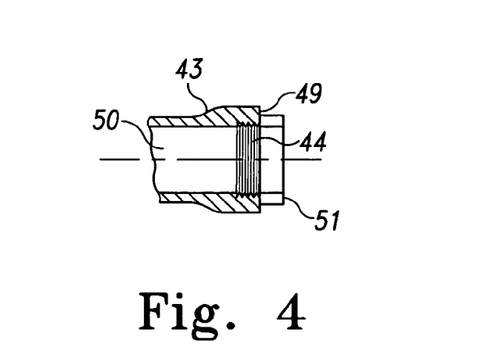
FIG. 4 is an enlarged detailed view of the distal end of the guide shaft of FIG. 3.
Figure 5:
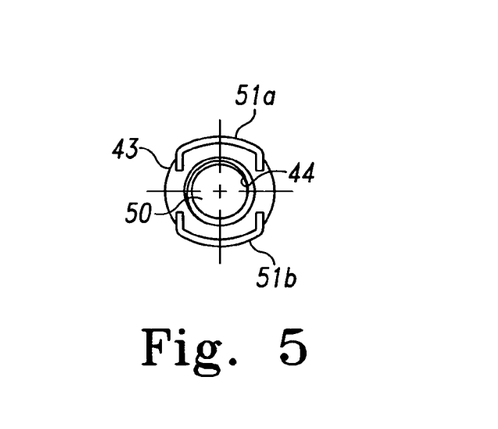
FIG. 5 is a right end elevation view of the guide shaft of FIG. 3.
Figure 12:
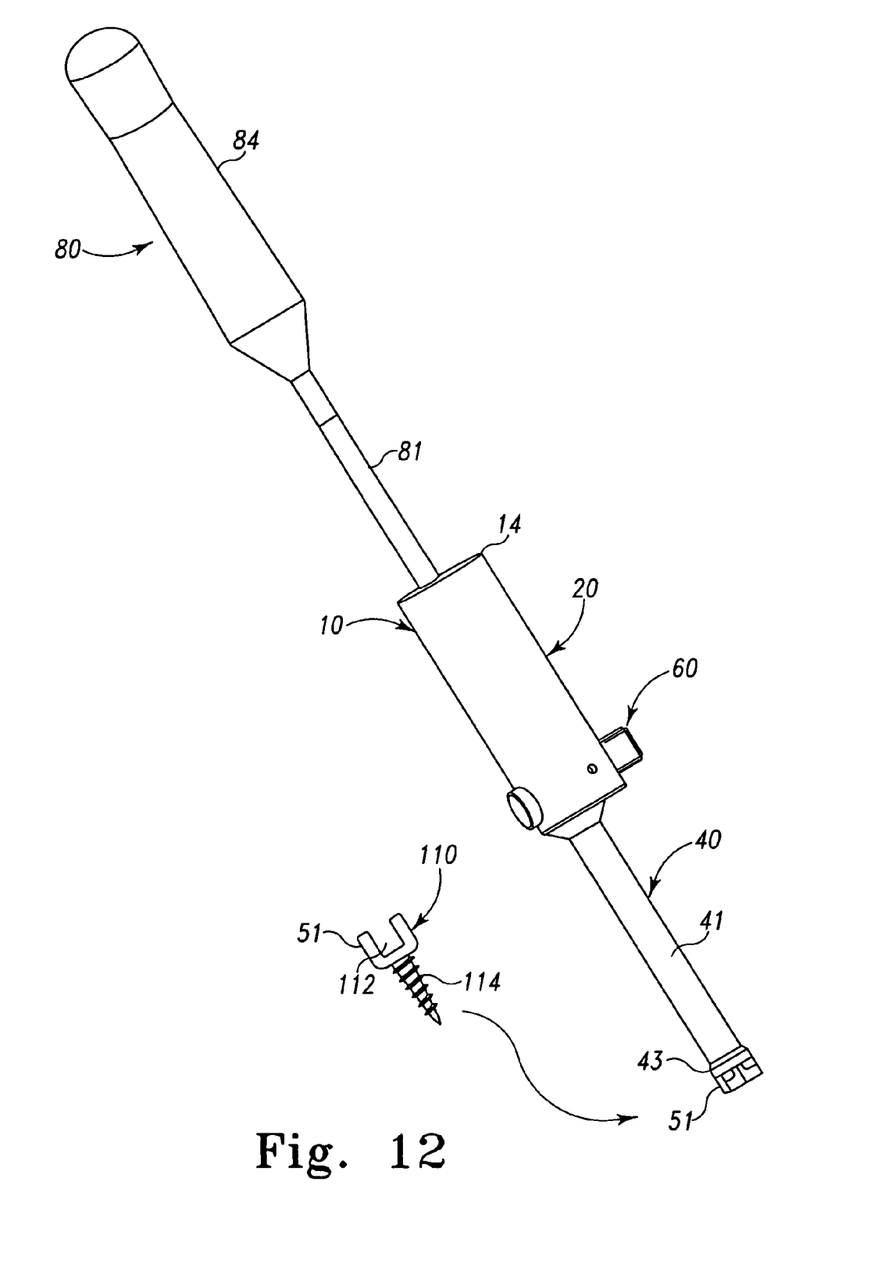
FIG. 12 is an elevation view of the delivery instrument of FIG. 1 positioned adjacent to a receiving member.

Guide shaft 40 is shown separated from delivery instrument 10 in FIG. 2 and secured to delivery instrument 10 in FIG. 1. As also shown in FIGS. 3-5, guide shaft 40 includes an internal longitudinal bore 50 defined by elongated body 41 and configured to receive an implant and a driver instrument, as first shown in FIG. 9. Longitudinal bore 50 extends between and opens at proximal end opening 42a and distal end opening 43a. Distal end 43 includes internal threaded portion 44 along a distal end portion of bore 50. The external wall of guide shaft 40 adjacent distal end 43 is flared outwardly to provide an increased wall thickness at distal end wall 49, as shown in FIG. 4. A flange 51 extends distally from distal end wall 49. In the illustrated embodiment, flange 51 includes first and second portions 51a, 51b located on opposite sides of end wall 49 about bore 50, as shown in FIG. 5. First and second portions 51a, 51b define a generally rectangular shape in the illustrated embodiment. The shape of flange 51 facilitates placement and engagement of delivery instrument 10 in a particular orientation and location with respect to a receiving member, such as shown in FIG. 12, and also guides an implant 100 to the implantation location.

Figure 6:
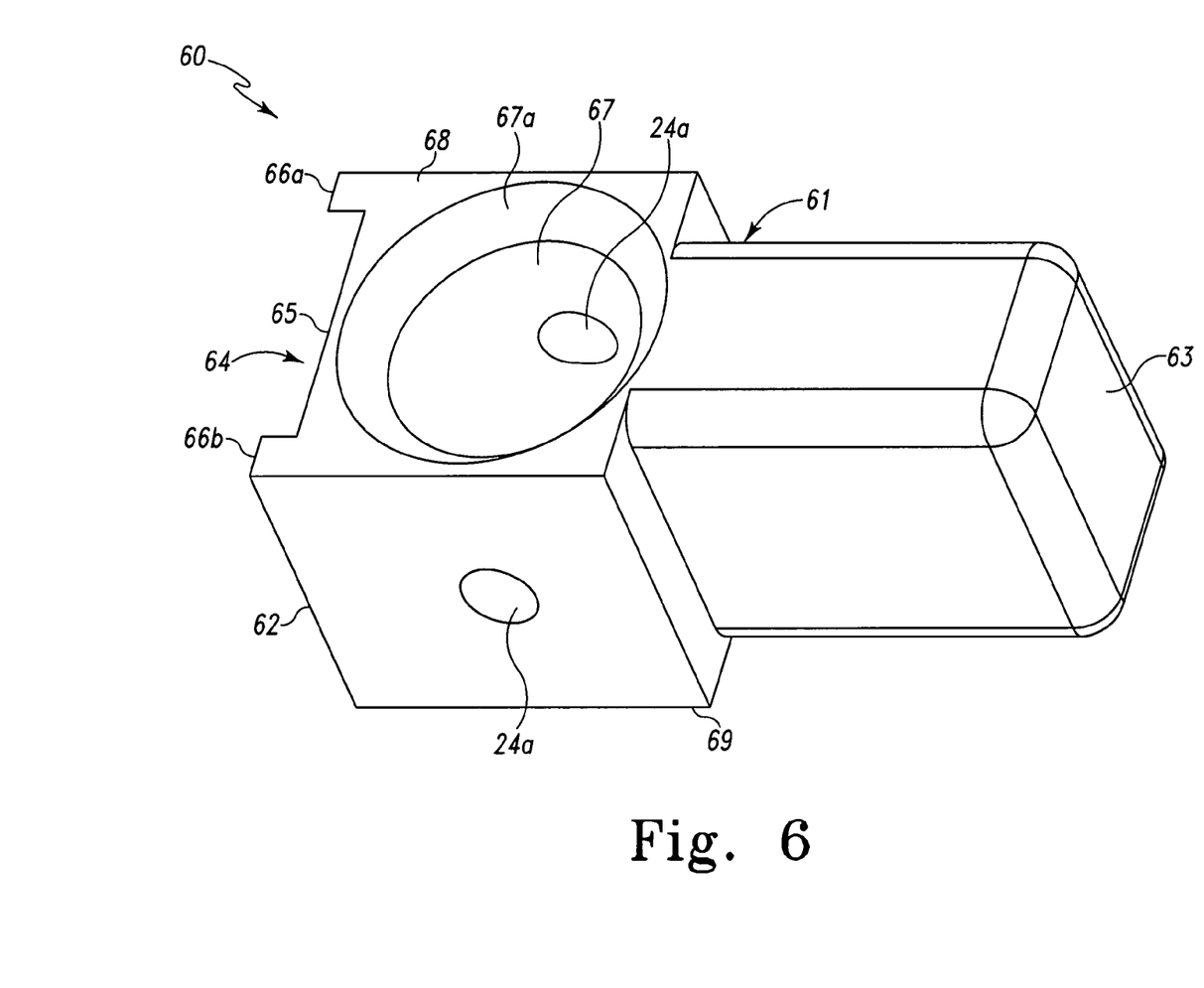
FIG. 6 is an enlarged detailed view of the actuating member of the delivery instrument in FIG. 1.

Referring now to FIG. 6 there is shown in perspective view actuating member 60 of instrument 10. Actuating member 60 includes a body 61 extending between a first end 62 opposite a second end 63. First end 62 is structured for placement within handle member 20 and is defined by a notched section 64 including end wall 65 disposed between a pair of projections 66a, 66b. Second end 63 is generally structured to project from handle member 20 to facilitate contact by a human operator, and in one or more embodiments may include one or more grip enhancing features. Actuating member 60 further includes an implant channel 67 extending between and opening through upper and lower surfaces 68, 69. At a position adjacent to upper surface 68, implant channel 67 includes a chamfered surface 67a structured to lead an implant 100 into alignment with implant channel 67. A pin hole 24a extends transversely through actuating member 60 and implant channel 67. When actuating member 60 is engaged with handle member 20, pin hole 24a may be brought in line with thru-hole 24. A pin or other locking device (not shown) may be placed in handle member 20 and actuating member 60 in holes 24, 24a to prevent actuating member 60 from moving and implant 100 from being loaded into implant channel 67. Furthermore, when pin hole 24a is brought in line with thru-hole 24, a human operator may visually inspect implant channel 67 to confirm the presence or absence of an implant 100 therein.

Figure 7:
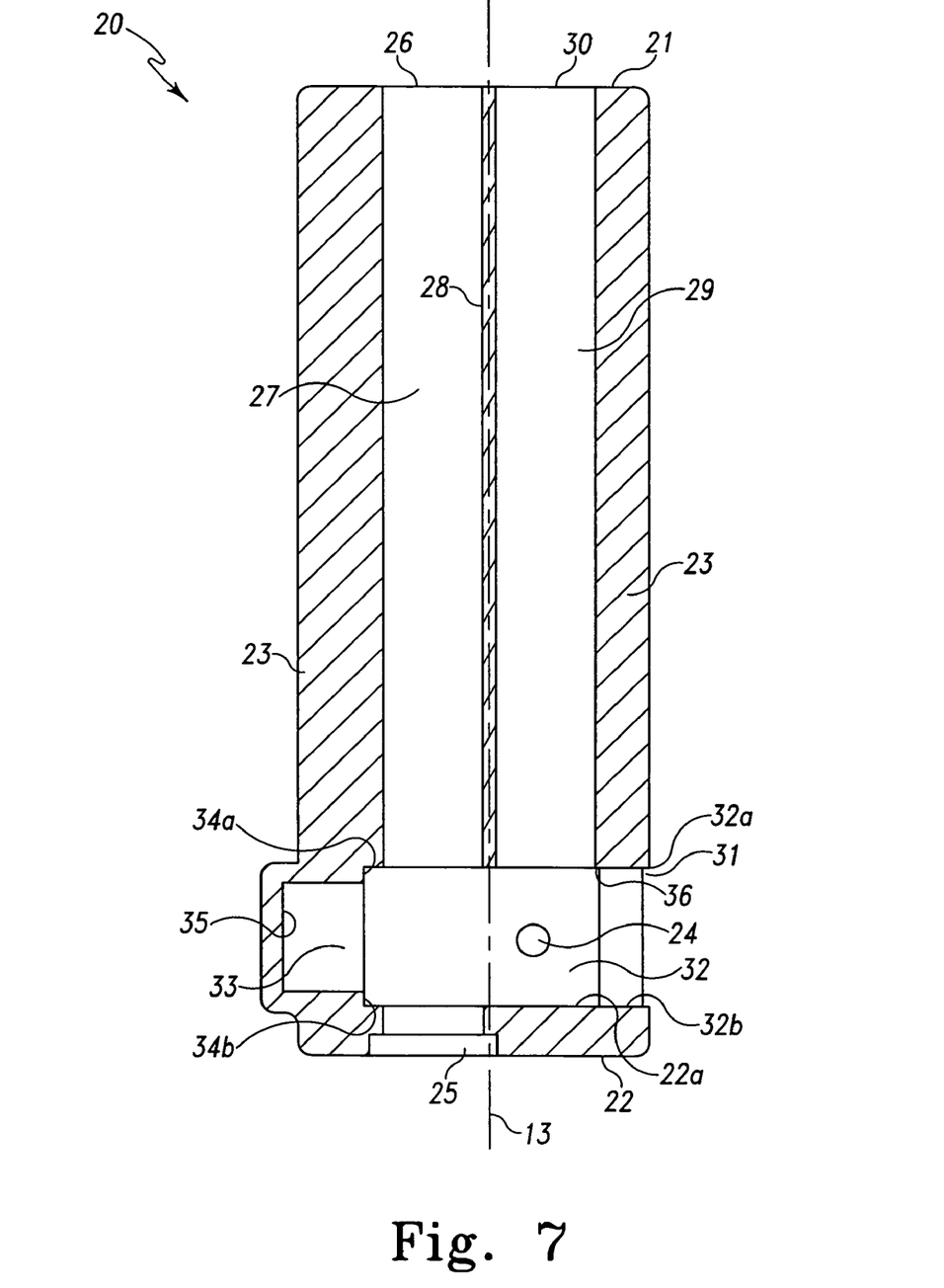
FIG. 7 is cross sectional view of the handle member of the delivery instrument of FIG. 2 viewed along line 7-7 of FIG. 2.

In FIG. 7 there is illustrated a longitudinal section view of handle member 20 along view line 7-7 in FIG. 2. Handle member 20 includes an instrument passage 27 extending longitudinally through handle member 20 from guide shaft engagement opening 25 at distal end wall 22 to instrument access port 26 at proximal end wall 21. Instrument passage 27 is formed adjacent to an implant compartment 29 but is separated therefrom by a barrier wall 28. Implant compartment 29 is defined by an implant loading port 30 extending through proximal end wall 21 and an internal surface 22a of distal end wall 22. Implant loading port 30 is generally structured to facilitate placement of implants 100 into implant compartment 29. In one form, implants 100 may be individually loaded into implant compartment 29. In an alternative non-illustrated form, implants 100 may be arranged in a pre-loaded clip or cartridge with implant compartment 29 correspondingly being structured to receive the pre-loaded clip or cartridge. When all of implants 100 have been dispensed, the empty clip or cartridge may be removed and replaced with another pre-loaded clip or cartridge. In yet another embodiment, implant loading port 30 is not provided. Implants are pre-loaded into implant compartment 29, and when all implants have been dispensed, the instrument is discarded or exchanged for another instrument. Alternatively, another handle member preloaded with implants may be engaged to guide shaft 40. In another form, instrument 10 may also include one or more implant compartments in addition to implant compartment 29. The one or more additional implant compartments may supply additional implants when the implants in other compartments are used.

A transverse opening 31 is formed in side wall 23 and provides an opening to transverse pocket 32, which extends transversely across implant compartment 29 and passage 27 to a truncated end portion 33 formed by ledge sections 34a, 34b disposed inwardly of terminal wall 35. The distal most part 32b of transverse pocket 32 is formed by internal surface 22a while the proximal most part 32a is formed by medial wall section 36. Transverse pocket 32 communicates with both instrument passage 27 and implant compartment 29 to provide a conduit for implants 100 to pass from implant compartment 29 to instrument passage 27.

Figure 8:
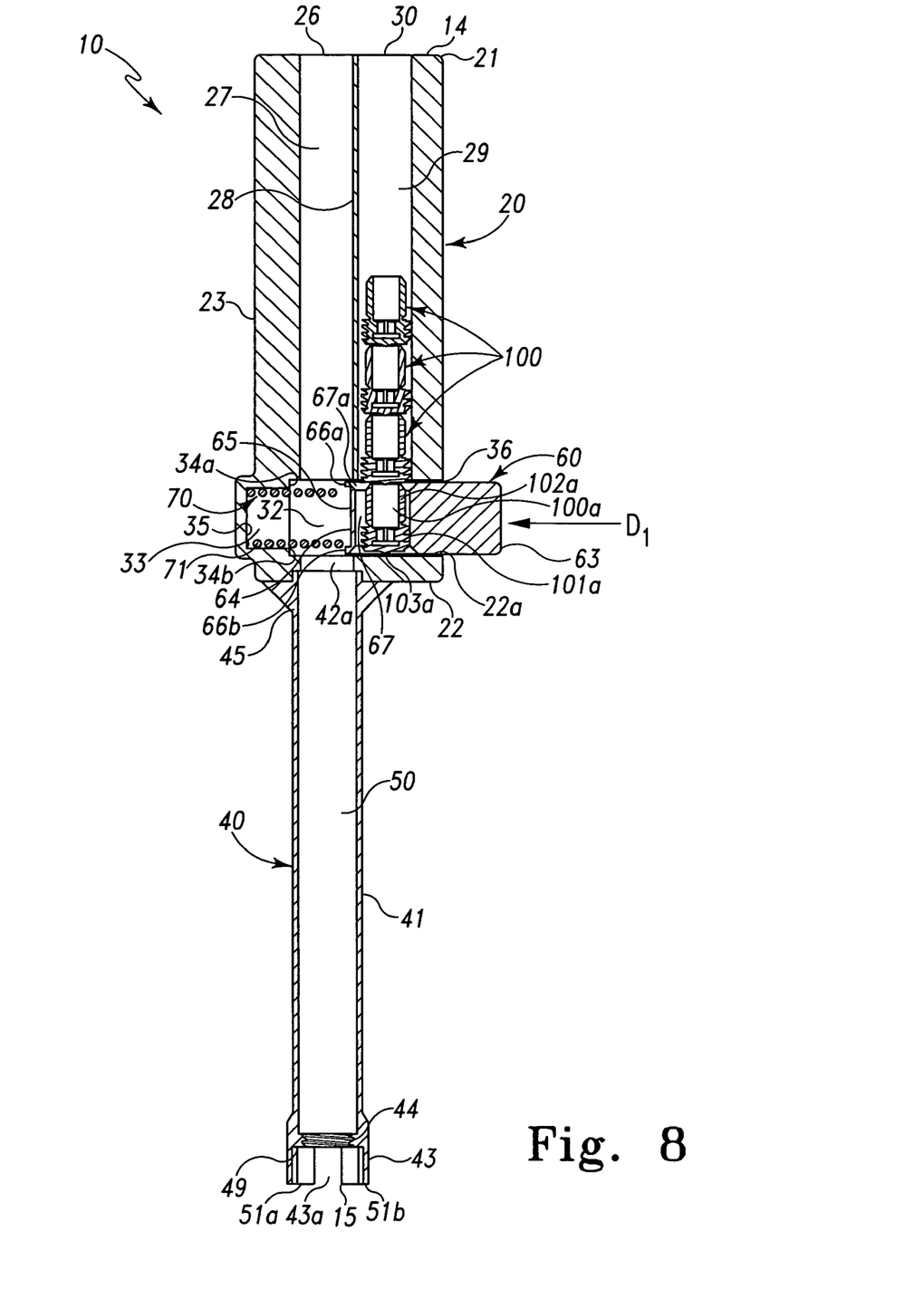
FIG. 8 is a cross sectional view of the delivery instrument of FIG. 1 viewed along line 8-8 of FIG. 1.
Figure 9:
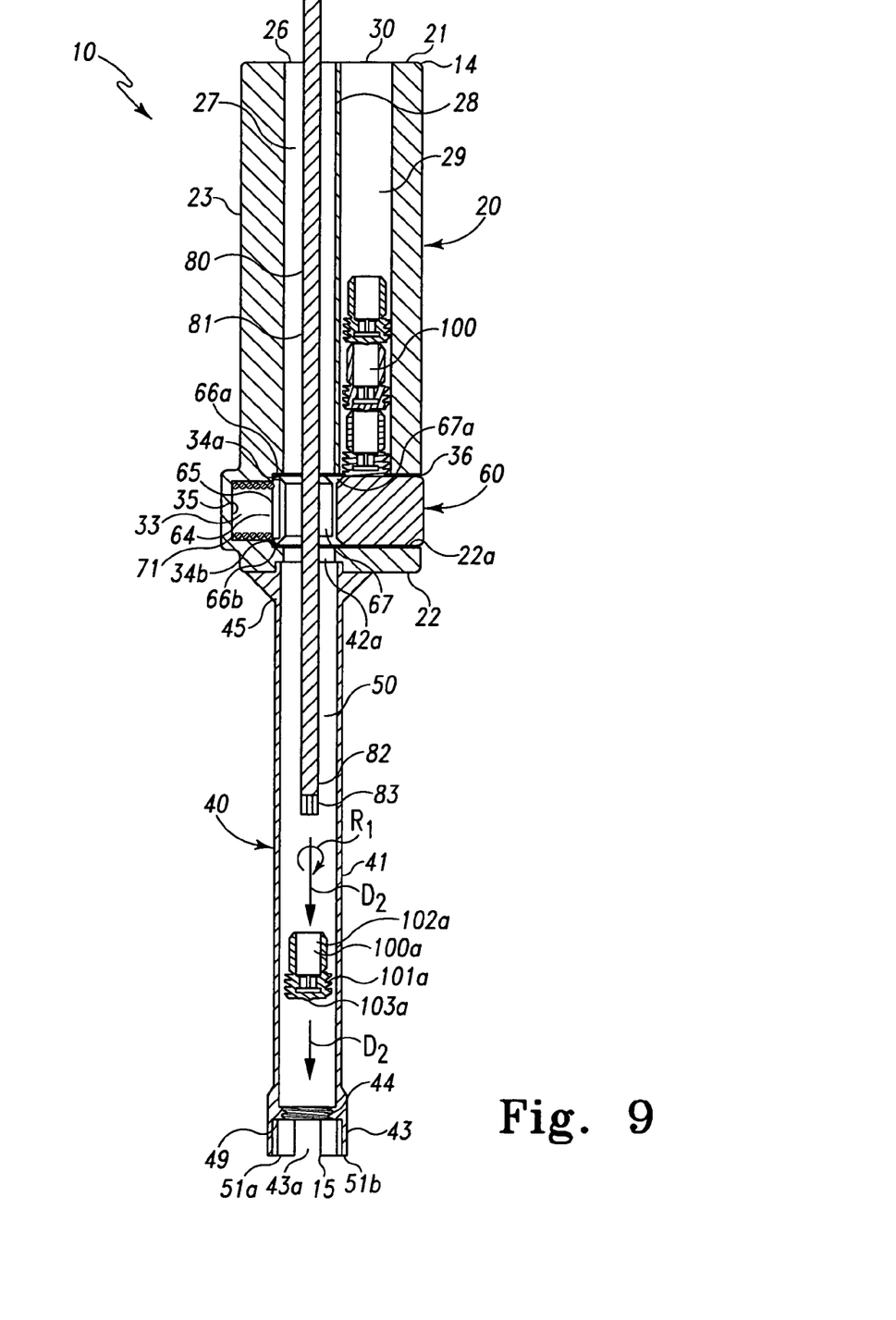
FIG. 9 is a cross sectional view of the delivery instrument of FIG. 1 viewed along line 8-8 of FIG. 1 with an implant driver.
Figure 10:
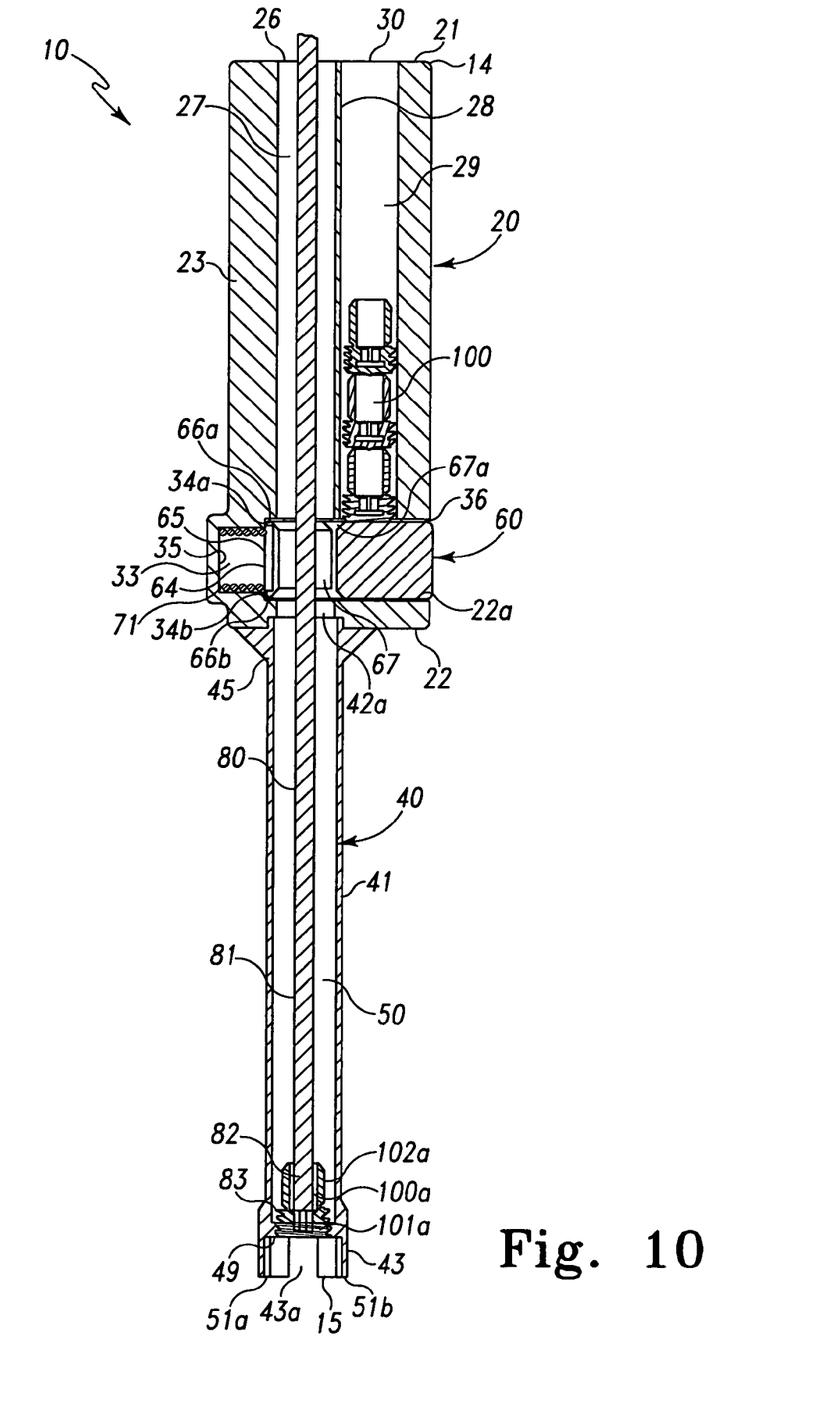
FIG. 10 is a cross sectional view of the delivery instrument of FIG. 1 viewed along line 8-8 of FIG. 1 with the implant driver and the actuating member depressed.

Referring now to FIGS. 8-10, there is shown in longitudinal section instrument 10 including a plurality of implants 100. A biasing member 70 in the form of a coil spring 71 has been placed in transverse pocket 32 between terminal wall 35 and actuating member 60. In other non-illustrated forms, biasing member 70 may be alternatively configured, like for example, as a leaf spring or a split washer, just to name a few possibilities. Coil spring 71 engages with end wall 65 at notched section 64 between projections 66a, 66b and forces implant channel 67 into alignment with implant compartment 29. Projections 66a, 66b are generally structured to provide a guide to retain coil spring 71 within transverse passage 32 and in contact with end wall 65. A first implant 100a, including a threaded stem portion 101a opposite a head portion 102a (FIG. 11), may then engage with chamfered surface 67a and be guided into implant channel 67 until point 103a contacts internal surface 22a and movement of the implant in a distal direction is stopped. Once first implant 100a has been loaded into implant channel 67 from implant compartment 29, a force may be applied to second end 63 to move actuating member 60 in direction $D_1$. As actuating member 60 is moved in direction $D_1$, coil spring 71 is compressed and projections 66a, 66b move toward contact with ledges 34a, 34b respectively. Once actuating member 60 contacts ledges 34a, 34b, movement in direction $D_1$ is stopped and implant 100a is aligned with instrument passage 27 and longitudinal bore 50. In this position, implant 100a passes through implant channel 67 and falls or slides toward distal end opening 43a of guide shaft 40 until it meets internal threading 44, as shown in progression in FIGS. 9 and 10. In other non-illustrated embodiments, it is contemplated that actuating member 60 may be alternatively biased. For example, in one non-limiting form, implant channel 67 may be biased into alignment with instrument passage 28 such that actuating member 60 must be moved in a direction opposite $D_1$ in order to receive an implant 100 in implant channel 67. In another form, biasing member 70 is absent from instrument 10 and a human operator must displace actuating member 60 between passage 28 and implant compartment 29.

Also shown in FIGS. 9 and 10 is the distal end 82 of an implant driver instrument 80 including a shaft portion 81 terminating at a tip portion 83 structured to engage with implants 100. As tip portion 83 is moved distally in direction $D_2$, it passes through implant channel 67, which may be kept in alignment with instrument passage 27 and longitudinal bore 50 by a continued application of force in direction $D_1$ by a human operator, in order to provide clearance for operation of driver instrument 80. In an alternative configuration however, a human operator may release the application of force in direction $D_1$ once driver instrument 80 has passed distally through implant channel 67. As coil spring 71 forces actuating member 60 and implant channel 67 back toward alignment with implant compartment 29, contact is made between actuating member 60 and driver instrument 80, stopping the movement of actuating member 60 while keeping implant channel 67 in sufficient alignment with instrument passage 27 and longitudinal bore 50 to permit use of driver instrument 80. In another embodiment, a locking device is provided to maintain actuating member 60 in the depressed position. In another embodiment actuating member 60 is rotatable or otherwise configured to engage handle member 20 to be secured in the depressed condition.

Internal threaded portion 44 of guide shaft 40 is structured to stop implant 100a before reaching distal end opening 43a. However, threaded stem portion 101a is structured to threadingly engage with internal threaded portion 44 to permit passage of implant 100a therethrough toward distal end opening 43a and the implantation location. Furthermore, tip portion 83 may engage with implant 100a while driver instrument 80 is rotated in direction $R_1$ to provide threaded engagement of threaded stem portion 101a with internal threaded portion 44, as shown in FIG. 10. Rotation of driver instrument 80 may continue until implant 100a has passed through internal threaded portion 44 and into engagement with the implantation location. In addition to retaining implant 100a within longitudinal bore 50, internal threaded portion 44 also provides delivery of implant 100a in a proper or desired orientation.

Figure 11:
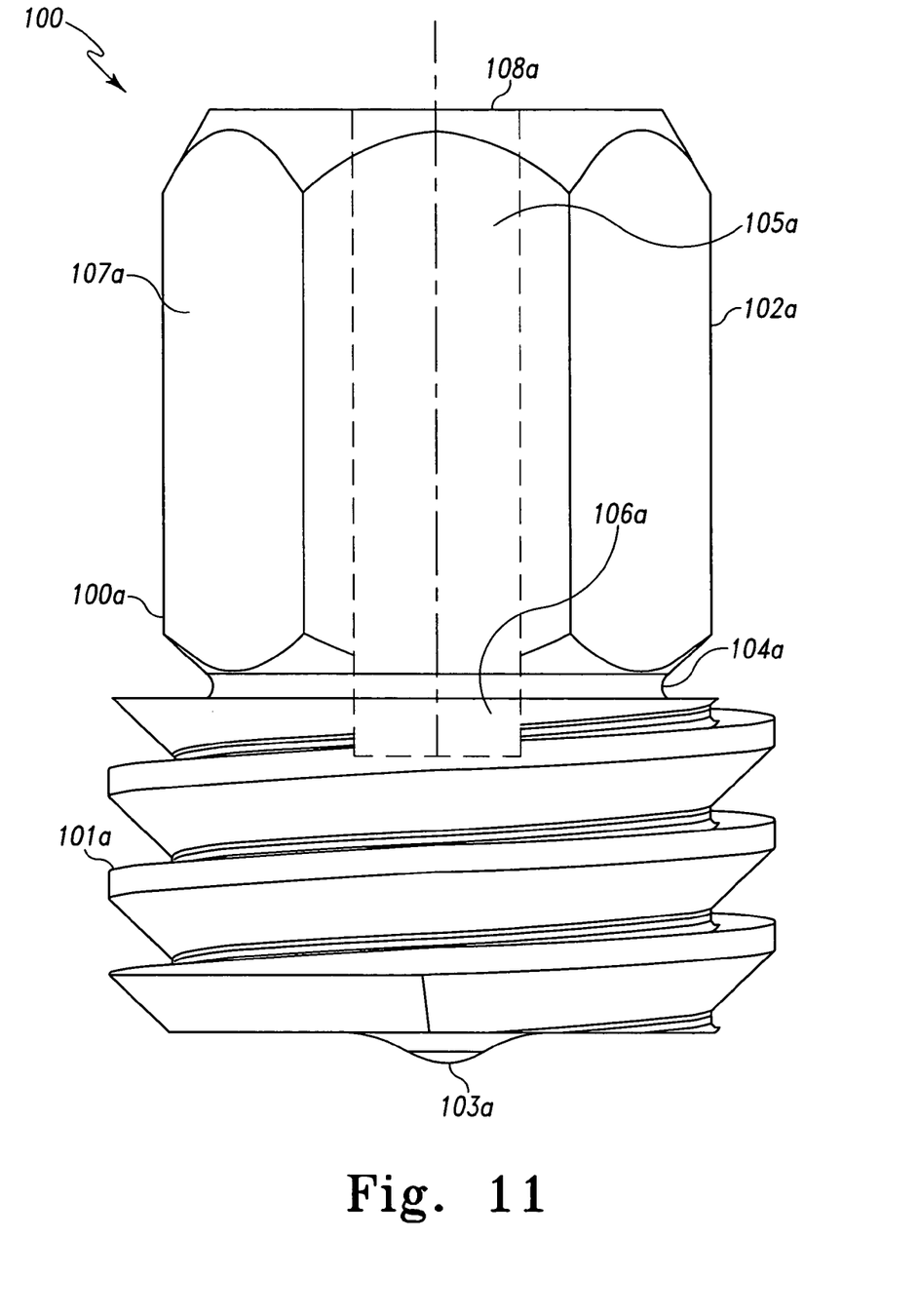
FIG. 11 is a side view of an implant deliverable with the instrument of FIG. 1.

In FIG. 11 there is shown in side plan view, with some features in phantom, implant 100a. Implant 100a includes externally threaded stem portion 101a opposite head portion 102a. In one embodiment, a break-off section 104a is disposed between head portion 102a and stem portion 101a. As the torque applied to head portion 102a reaches a threshold, head portion 102a severs relative to the threaded stem portion 101a at break-off section 104a. In this embodiment, driver instrument 80 can be used in conjunction with delivery instrument 10 to engage proximal tool engagement portion 106a through recess 105a to provisionally engage implant 100a at the implantation location. After removal of the delivery instrument 10, another instrument may then be engaged with surfaces 107a of head portion 102a to apply the threshold level of torque to sever head portion 102a from stem portion 101a and to remove head portion 102a from the implantation location. Still other embodiments contemplate that the implant only includes a threaded portion for engaging the receiving member without any break-off section or any head portion. Implant 100a also includes a distal tip 103a structured to positively engage and penetrate the receiving member or another implant. Tip 103a can also be received in recessed surface 108a of an adjacent implant 100 to maintain vertical alignment of implants 100 in implant compartment 29. It should be appreciated that each of implants 100 in FIGS. 8-10 includes the features as described in relation to implant 100a in FIG. 11, although embodiments having different features are also contemplated.

Delivery instrument 10 can be positioned adjacent a receiving member 110, such as shown in FIG. 12, to receive implants 100 when dispensed therefrom. In the illustrated embodiment, receiving member 110 includes an internally threaded receptacle 112 to receive threaded stem portion 101a of implant 100a. As threaded stem portion 101a exits guide shaft member 40, it comes into contact with receptacle 112 of receiving member 110. Flange 51 can engage receptacle 112 to maintain alignment of delivery instrument 10 therewith, reducing any potential for cross-threading of implants 100 in receptacle 112. Driver instrument 80 including operator handle 84 maintains engagement with implant 100a in head portion 102a as threaded portion 101a is distally advanced from the distal end 43 of guide shaft member 40. Further rotation of shaft 81 with operator handle 84 rotates implant 100a and threadingly engages it to receptacle 112 of receiving member 110. When implant 100a is seated in receiving member 110, driver instrument 80 may be removed from delivery instrument 10 and implant channel 67. Actuating member 60 is released to align channel 67 with implant compartment 29 to receive a second one of implants 100, as described in relation to FIGS. 8-10. Delivery instrument 10 can be relocated to a second receptacle of receiving member 110, or to a receptacle of another receiving member, for securement of the second implant 100 thereto. The process can be repeated until the desired number of implants have been delivered, or until all implants have been delivered from delivery instrument 10.

Receiving member 110 can be an implant engageable to bony structure of the patient, such as a spinal plate, a bone screw, a clamp, an interbody device, or any other construct structured to receive an implant. For example, in FIG. 12 receiving member 110 includes threaded shaft 114 like a bone screw to secure it to the bony structure. Implant 100 is positioned in receptacle 112 to engage a spinal rod or other implant in receptacle 112. In another example, the receiving member is a bone plate and is configured to receive one or more screws. Implants 100 secure the one or more screws to the plate to prevent screw backout. In another specific application, the implant is engaged to one or more bony elements of the spinal column. In another embodiment, implant 100 is structured for engagement directly to bony or soft tissue of the patient.

While implants 100 illustrated in association with instrument 10 include a threaded portion, it is contemplated that one or more alternative implants may be used with instrument 10, including ones in which a threaded portion is absent. For example, one or more implants deliverable with instrument 10 may be engageable with an implanted receiving member through a friction or press fit engagement, a slot and key configuration, a ball and socket configuration or by adhesion or fusion, just to name a few possibilities. Additionally, it should be appreciated that alternative configurations of instrument 10 are contemplated to prevent implants deliverable therewith from exiting guide shaft 40 in lieu of internal threaded portion 44. In one non-illustrated form longitudinal bore 50 of guide stem 40 may include a tongue or lip by which an implant may pass upon reaching a threshold level of force as applied by, for example, driver instrument 80. In another form, implant channel 67 of actuating member 60 may include one or more retaining elements structured to retain an implant therein until forced therefrom by driver instrument 80. In another form, it is contemplated that instrument 10 lacks any retaining structure and that guide stem 40 is aligned with an implanted receiving member before an implant is positioned into alignment with guide shaft 40 from implant compartment 29.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A surgical system, comprising:
a receiving member implantable in a patient, the receiving member including at least one receptacle;
an instrument including a handle member extending along a longitudinal axis from a proximal end to a distal end, the handle member defining a passage and a compartment extending therein in side-by-side relation from the proximal end toward the distal end, an actuating member extending transversely across the passage and the compartment adjacent to the distal end, and a guide shaft engaged with and extending distally from the handle member, the guide shaft being axially aligned with the passage;
wherein the actuating member is structured to move an implant of a plurality of implants positioned in the compartment to the passage into alignment with the guide shaft where the implant is fed toward a distal end of the guide shaft, the implant being engageable in the receptacle of the receiving member when delivered from a distal end of the guide shaft; and a spinal rod positionable in the receptacle and engageable by the implant to secure the spinal rod in the receptacle.

2. The system of claim 1, wherein the handle member further includes an elongated side wall extending between the proximal end and the distal end, the side wall including an opening defining a transverse bore to receive the actuating member in a moveable relationship.

3. The system of claim 2, wherein the actuating member includes an internal end opposite an external end, the external end being structured for engagement by a human operator to move the actuating member along the transverse bore.

4. The system of claim 3, further comprising a biasing member, the biasing member being structured to influence the actuating member across a plurality of positions in the transverse bore.

5. The system of claim 1, wherein the actuating member is transversely slidable within a transverse bore between a loading position where an implant channel of the actuating member is aligned with the compartment to receive an implant from the compartment and a delivery position where the implant channel is aligned with the passage to deliver the implant to the guide shaft.

6. The system of claim 5, further comprising a biasing element structured to influence the actuating member to one of the delivery position and the loading position.

7. The system of claim 6, wherein the biasing element is compressible to facilitate movement of the actuating member to the delivery position.

8. The system of claim 1, wherein the receiving member is engageable to a bony structure of the patient and the implants are engageable in the at least one receptacle.

9. The system of claim 8, wherein the guide shaft includes an internally threaded portion adjacent a distal end opening, the implant threadingly passing through the internally threaded portion of the guide shaft for delivery through the distal end opening of the guide shaft.

10. The system of claim 1, wherein the guide shaft includes a tubular member with a longitudinal bore extending co-axially with the passage and further includes a flange extending distally from a distal end wall of the guide shaft, the flange being positionable in contact with the receiving member adjacent the receptacle.

11. A surgical system, comprising:
an instrument including an elongated handle member, a guide shaft engaged with and extending distally from the handle member along a longitudinal axis, and an actuating member coupled with the handle member and extending transversely across the handle member, the actuating member communicating with a compartment and a passage defined by the handle member with the passage and the compartment extending along the longitudinal axis in the handle member and in side-by-side relation from a proximal end of the handle member toward a distal end of the handle member, the actuating member being slidable between the passage and the compartment to individually deliver respective ones of a plurality of implants stored in the compartment from the compartment to the passage wherein the passage is aligned with the guide shaft;
a driver instrument positionable within the passage and through the guide shaft to engage the respective implant in the guide shaft a receiving member implantable in a patient, the receiving member including at least one receptacle for receiving at least one of the plurality of implants therein; and a spinal rod positionable in the receptacle and engageable by the implant to secure the spinal rod in the receptacle.

12. The system of claim 11, further comprising a receiving member implantable in a patient, the receiving member including at least one receptacle for receiving at least one of the plurality of implants therein.

13. A surgical instrument for delivering multiple implants to an implantation location, comprising:
a handle member including a side wall extending longitudinally from a proximal end wall to a distal end wall, the handle member defining an internal bore extending therethrough from the proximal end wall to the distal end and a dividing wall separating the internal bore from at least one implant compartment in the handle member, the implant compartment and the internal bore communicating with a transverse pocket extending through the side wall at a side wall opening;
a guide shaft engaged with and extending distally from the distal end wall of the handle member along a longitudinal axis, the guide shaft including an internal bore aligned with the internal bore of the handle member, the internal bore of the guide shaft extending to a distal end opening;
an actuating member defining an implant channel, the implant channel being structured to individually house a respective implant of a plurality of implants stored in the implant compartment and wherein the actuating member is translatable in the transverse pocket between a receiving position where the implant channel is aligned with the implant compartment for receiving the respective implant to a delivery position where the implant portion is aligned with the internal bore for delivering the implant to the internal bore of the guide shaft a receiving member implantable in a patient, the receiving member including at least one receptacle for receiving at least one of the plurality of implants therein; and a spinal rod positionable in the receptacle and engageable by the implant to secure the spinal rod in the receptacle.

14. The instrument of claim 13, wherein a driver instrument is positionable within the internal bore when the actuating member is at the second position to advance the implant toward the distal end opening of the guide shaft, the driver instrument being structured to engage the implant with a retaining portion of the guide shaft for delivery through the distal end opening.

15. The instrument of claim 13, further comprising a biasing member disposed in the transverse pocket to influence the actuating member to the first position and wherein the biasing member is actuated when the actuating member is in the second position.

16. The instrument of claim 13, wherein the implants are structured to engage a receptacle of a receiving member engaged to a bony structure of a patient.

17. The instrument of claim 13, wherein the guide shaft includes a flange extending distally from a distal end wall of the guide shaft, the flange being positionable in contact with a receiving member engaged at the implantation location, the receiving member including at least one receptacle structured to accept the implant.

18. The instrument of claim 13, wherein the internal bore of the guide shaft is elongated along the longitudinal axis from the distal end opening of the guide shaft to the internal bore of the handle member and the compartment and internal bore of the handle member are each elongated and extend along the longitudinal axis in the handle member.

19. The instrument of claim 11, wherein the compartment and the passage of the handle member each extend in a direction paralleling the longitudinal axis.

20. The instrument of claim 1, wherein the compartment and the passage of the handle member are each elongated along the longitudinal axis and extend in side-by-side relation in a direction paralleling the longitudinal axis.

* * * * *